United States Patent
Wesselmann et al.

(10) Patent No.: US 10,780,253 B2
(45) Date of Patent: Sep. 22, 2020

(54) METHOD FOR PRODUCING A BALLOON FOR ANGIOPLASTY

(71) Applicant: BIOTRONIK AG, Buelach (CH)

(72) Inventors: Matthias Wesselmann, Ruedlingen (CH); Semijan Hani, Beulach (CH); Bodo Quint, Dettighofen (DE)

(73) Assignee: BIOTRONIK AG, Buelach (CH)

( * ) Notice: Subject to any disclaimer, the term of this patent is extended or adjusted under 35 U.S.C. 154(b) by 490 days.

(21) Appl. No.: 15/500,848

(22) PCT Filed: May 21, 2015

(86) PCT No.: PCT/EP2015/061272
§ 371 (c)(1),
(2) Date: Jan. 31, 2017

(87) PCT Pub. No.: WO2016/026591
PCT Pub. Date: Feb. 25, 2016

(65) Prior Publication Data
US 2017/0216566 A1    Aug. 3, 2017

Related U.S. Application Data

(60) Provisional application No. 62/039,439, filed on Aug. 20, 2014.

(30) Foreign Application Priority Data

Aug. 20, 2014 (EP) .................................... 14181572

(51) Int. Cl.
*B29C 49/48* (2006.01)
*A61M 25/10* (2013.01)
(Continued)

(52) U.S. Cl.
CPC ...... *A61M 25/104* (2013.01); *A61M 25/1029* (2013.01); *A61M 29/02* (2013.01);
(Continued)

(58) Field of Classification Search
None
See application file for complete search history.

(56) References Cited

U.S. PATENT DOCUMENTS 6,089,854 A * 7/2000 Outreman ............... B29C 49/48
425/526
7,771,450 B2    8/2010 Tomaschko et al.
(Continued)

FOREIGN PATENT DOCUMENTS

EP    1620160 B1    3/2010

OTHER PUBLICATIONS

Lang, Ulrich, "Notification of Transmittal of the International Search Report and the Written Opinion of the International Searching Authority, or the Declaration", Patent Cooperation Treaty Application No. PCT/EP2015/061272, European Patent Office as the International Searching Authority, International Search Report Completed Aug. 13, 2015, International Search Report dated Aug. 24, 2015, 8 Pages.

(Continued)

*Primary Examiner* — Monica A Huson
(74) *Attorney, Agent, or Firm* — Greer, Burns & Crain, Ltd.; Steven P. Fallon (57) ABSTRACT

A method for producing a balloon from a suitable blank is provided. The blank is introduced into an outer mold heated an first expanded to expand it against the inner wall of the outer mold. Pressure is reduced to relax the blank away from the inner wall. The three-dimensional volume of the mold is changed. Second expanding of the blank expands again against the inner wall of the changed volume of the outer (Continued)

mold. Balloons of the invention consist of a middle cylindrical region and two end regions delimiting the middle cylindrical region. With a pressure application of 6 bar, a ratio of the cross section in the middle region to the cross section in the end region is at least 2, and preferably greater than 3.

17 Claims, 4 Drawing Sheets

(51) Int. Cl.
    *B29C 49/18*     (2006.01)
    *A61M 29/02*     (2006.01)
    *B29L 31/00*     (2006.01)
    *B29C 49/00*     (2006.01)
    *B29K 105/00*     (2006.01)

(52) U.S. Cl.
    CPC ............ *B29C 49/18* (2013.01); *B29C 49/185* (2013.01); *B29C 49/48* (2013.01); *B29C 2049/0089* (2013.01); *B29C 2049/4879* (2013.01); *B29K 2105/253* (2013.01); *B29L 2031/7543* (2013.01)

(56) References Cited

U.S. PATENT DOCUMENTS

| | | |
|---|---|---|
| 2001/0008661 A1 | 7/2001 | Jung, Jr. |
| 2002/0125617 A1 | 9/2002 | Skinner |
| 2011/0285059 A1 | 11/2011 | Hennessy |

OTHER PUBLICATIONS

Muller, Gérard, "Extended European Search Report", European Patent Application No. EP 14181572.0, European Patent Office, Search Completed Feb. 23, 2015, dated Mar. 3, 2015, 5 pages.

\* cited by examiner

METHOD FOR PRODUCING A BALLOON FOR ANGIOPLASTY

The present invention relates to a method for producing a balloon from a suitable blank. The invention further relates to a balloon, which is suitable for use with a catheter in angioplasty.

BACKGROUND

Angioplasty, also referred to as transluminal angioplasty, is a method for widening or re-opening constricted or closed blood vessels (usually arteries, sometimes veins) through balloon dilation in the vessel or other methods (laser, thrombectomy catheter, etc.).

The balloon catheters are almost always placed into the stenosis (constriction) from the groin via a guide wire and guide catheter and are inflated with pressure (7-30 bar), and the constriction is usually eliminated as a result and an operation is avoided. In addition, stents (wire meshes that support the vessel from the inside and are intended to hold the vessel open) are often implanted (stent angioplasty).

The balloon catheters of this type, at their distal end region (within the scope of this application the term "distal" is used in the sense of remote from the user), have a balloon, which is acted on by a pressurized fluid and which is thus expanded (dilated). Due to the expanding balloon, the constricted bodily vessels are widened again or opened again. A support structure (stent) can also be fitted on such balloons and is then implanted by the expansion of the balloon at the formerly constricted site.

Such a balloon consists of a substantially cylindrical region in the middle and two conical end regions (often also referred to as neck regions), where the balloon is connected to the catheter, in particular the lumen for applying fluid to the balloon. The terms "radial" and "axial" are used within the scope of the application accordingly. The term "axial" denotes the direction along the axis of symmetry of the substantially cylindrical middle region of the balloon, whereas the term "radial" accordingly denotes the direction of the radius from the cylinder axis to the balloon wall. The axial direction also corresponds to the axial direction of the catheter.

Such methods and balloon catheters are known in general and are used widely. Balloon catheters are used not only to treat constrictions in arteries, but also to implant artificial heart valves and support structure thereof.

In the simplest method according to the prior art, known a blow molding, a blank made of a suitable material is introduced into a mold, heated to a temperature above the glass transition temperature and acted on with pressure. The blank thus expands to the three-dimensional geometry of the mold. The blank is then cooled below glass transition temperature and the balloon is created. In the case of blow molding, the molded balloon neck cannot be smaller than the outer diameter of the blank.

Generally, substantially cylindrical tubes with two opposite conical end pieces are used as a mold. However, the mold may also consist of one piece, for example drawn glass molds, or also can be produced from two mold halves made of metal divided in the axial direction.

Stretch blow molding is a modified blow molding method, in which the molding process is triggered by an additional axial load on the blank. In this process variant, the blank can be thermomechanically drawn beforehand at its ends. It then has, at its ends, a much smaller diameter than in the middle and can thus be introduced into cones via the smaller neck diameter. The constricted balloon tube ends can be grasped outside the mold by the balloon molding system in order to draw the blank. The neck outer diameter of the balloon can thus be smaller than the blank outer diameter. This blank is introduced into the mold, fixed and heated after the above-described blow molding method and acted on with pressure.

The blank is a tube made of suitable plastic material. All thermoplastic materials that allow a sufficiently high elongation and provide sufficient strength in the biaxially drawn state are suitable materials. Successful examples include: polyamides and polyether block amides, polyurethanes, polyvinyl chloride, PET (polyethylene terephthalate), but also PEEK (polyether ether ketone). Sometimes such blanks are referred as parison in the literature.

In the case of the blow molding, the blank must endure enormous elongations in order to copy the balloon mold. In the case of angioplasty balloons, the radial elongation (referred to hereinafter as radial stretching) for the inner surface of the blank for polyamides lies in the range from 500% to 800%. The simultaneous axial elongation (referred to hereinafter as axial stretching) is given from the properties of the blank and in the case of blow molding can be controlled only within relatively narrow limits.

In the case of blow molding of balloons with a method of this type according to the prior art, it is inevitable that the resultant balloon has a much higher wall thickness at the conical end regions than in its middle and in the substantially cylindrical region. This is particularly because the balloon wall thickness with assumed material constancy of blank and balloon must be reciprocal relative to the balloon radius.

In the case of angioplasty, the balloon is introduced into the bodily vessel in the relaxed (deflated) state and is advanced to the site to be treated, for example the constriction. Accordingly, the thicker wall thickness in the conical end regions in the case of a balloon according to the prior art contributes substantially to the total diameter of the catheter. A high total thickness of a catheter, however, is disadvantageous when guiding the catheter, particularly in the case of narrow and winding bodily vessels.

Numerous production methods for such balloons are known in the prior art, of which the objective is to thin out the conical end regions (also often referred to as neck region), that is to say to remove material in these regions.

U.S. Pat. No. 7,771,450 describes a method for producing a balloon, wherein material is removed by laser ablation in the conical end regions.

EP1620160 describes a method where the wall thickness of the conical end regions is reduced by a means of laser ablation, mechanical abrasion or chemical etching.

However, all such methods of the prior art have the disadvantage that the material removal in the conical end regions is very difficult to control and that, in addition, local imperfections in the balloon structure are formed by the subsequent thermal or mechanical local treatments and lead to a lower pressure load-bearing capacity of the balloon.

SUMMARY OF THE INVENTION

A preferred method for forming a balloon for a balloon catheter from a blank that is in an outer mold includes heating the blank and first expanding with pressure to expand it against the inner wall of the outer mold,
after said first expanding, reducing pressure following expansion of the blank to relax the blank away from the inner wall, after said reducing, changing the three-dimensional volume of the mold, and after said changing, second expanding the blank with pressure again to expand it against the inner wall of the changed volume of the outer mold.

A preferred embodiment balloon suitable for use in a catheter for carrying out a method for angioplasty, consists of a middle cylindrical region and two end regions delimiting the middle cylindrical region. The balloon, with a pressure application of 6 bar, has a ratio of the cross section in the middle region to the cross section in the end region of at least 2, and preferably greater than 3.

BRIEF DESCRIPTION OF THE DRAWINGS

In the following, the invention is explained in further detail by way of example with the help of the exemplary embodiments shown in the drawings. Shown in schematic representation are FIGS. 1A-1D schematically show the method according to the invention in principle.

DETAILED DESCRIPTION OF THE PREFERRED EMBODIMENTS

Methods for producing and balloons of the invention have a middle cylindrical region that is stretched axially to a lesser extent than balloons produced according to the methods discussed in the background. In preferred methods of the invention, the contact with the hot mold wall in the fourth step ensures a reduction of the frozen stresses, as in the known blow molding methods, and thus ensures a stabilization of the balloon geometry. The heating and pressure application in the first step are preferably selected in such a way that the yield stress of the blank is exceeded.

The present inventors have determined that the primary cause for undesirable higher wall thickness in the conical end regions with a balloon from a blow molding method according to the prior art is the fact that the balloon wall thickness with assumed material constancy of blank and balloon is reciprocal relative to the balloon radius. However, the inventors have also identified that blank material is additionally removed from the balloon mold by the axial stretching. This makes the balloon additionally thinner in the cylindrical region, since the axial stretching in large regions increases proportionally to the radial stretching.

In accordance with the invention, the correlation of axial and radial stretching in the balloon molding method according to the invention is therefore changed selectively. This occurs in accordance with the invention because the severely radially stretched region (in the middle cylindrical part of the mold) is stretched axially to a lesser extent. Preferred methods of the invention leverage the viscoelastic properties of the blank, which is not yet cooled and is still heated, during the second pressure application and the associated change of the correlation between axial and radial stretching The change of the correlation between axial and radial stretching is implemented by the modification of the three-dimensional expansion of the outer mold and the renewed application of pressure to the heated blank in the three-dimensionally changed mold. The changed outer mold changes the correlation between radial and axial stretching. Within the scope of the invention, a modification of the three-dimensional volume of the outer mold is understood to mean that the outer mold is changed in such a way that the three-dimensional space, which in principle can be taken up in the mold by the blank, which is acted on with pressure, is changed. In principle, the inner surface of the outer mold must be changed accordingly. Due to the change according to the invention of the correlation between radial and axial stretching, there is no need to thin out material in the predefined regions of the balloon in a subsequent step. The method according to the invention, put more simply, ensures that, during the blow molding process, less material flows into certain regions than in a method according to the prior art. More material is held within the mold compared with the prior art.

The blow molding method according to the invention can also be configured as a stretch blow molding method, that is to say, during the method according to the invention, an additional tensile force can be exerted on the blank in an axial direction (for example by means of a weight).

The length of the mold is preferably reduced to produce the changed volume. The simple change of the axial expansion of the outer mold (reduction of the length of the mold) during the second pressure application leads to a more uniform distribution of the material compared with a blow molding method according to the prior art. Above all, the wall thickness in the middle cylindrical regions can thus be increased at the cost of the wall thickness in the conical end region compared to a balloon produced by a blow molding method according to the prior art. The need for a mechanical post-processing of the conical end or neck regions and the associated disadvantages are therefore eliminated.

This preferred embodiment of the method according to the invention leads to a particularly homogenous material distribution in a balloon thus produced of the type mentioned in the introduction. In a method according to the prior art, the conical end regions have a higher wall thickness than the cylindrical middle region. In the conical end regions, more material is left in a method according to the prior art than is desired. This has to be removed again subsequently in the case of a balloon produced by a method according to the prior art. The preferred embodiment of the method according to the invention follows a completely contrary principle. Due to the change of the three-dimensional volume of the mold in the third step and the additional pressure application in the fourth step, a homogenization of the material distribution is achieved.

Following the pressure application of the blank in the first step and the subsequent pressure relief, the blank contracts axially and radially very severely in the second step. The change of the three-dimensional extent of the mold in the third step takes this contraction into account. The blank is accordingly shaped to the changed three-dimensional mold in the fourth step. During these four steps of the method according to the invention, the blank continues to be at a temperature above the glass transition point. Accordingly, the material is very resilient here. Due to the change of the three-dimensional expansion of the mold (in particular of the mold length), the axial stretching in the cylindrical region can be considerably reduced during the second inflation of the balloon. The wall thickness in this region thus increases accordingly.

The balloon produced in accordance with the invention in this way has a much better stress distribution than conventional balloons, since the cones and necks having thicker walls due to the forming process can be re-formed so as to be thinner without weakening the cylindrical region. This leads to a balloon cone that can be better folded and therefore leads to much smaller folded balloon profiles. In addition, there is much less material in the conical end regions with constant wall thickness in the middle compared with the prior art, and therefore the overall catheter system is less rigid. The combination of the smaller diameter and the lower rigidity allows a much simpler and gentler guidance of the balloon catheter by the handler, in particular when the site of treatment and therefore the target site of the balloon is situated in a very winding bodily vessel with a small diameter. At the same time, the balloon produced in accordance with the invention folds together back into its relaxed form much more easily following expansion at the treatment site than a balloon according to a production method according to the prior art.

The inflatability of balloon tubes is subject to natural limits with predefined tube outer diameter. The inflation pressure also has to be able to be fed on the tube inner surface, which makes it possible to increase the stress in the thermally softened blank wall to such an extent that the material starts plastically to form a balloon. A further increase of the balloon wall thickness is therefore only possible with a method according to the prior art by increasing the outer diameter of the tube. The method according to the invention provides the possibility of achieving an additional increase of the balloon wall thickness of more than 10% (preferably up to 30%) in the middle cylindrical region of the balloon by the reduction of the axial stretching during the second forming and annealing.

Within the scope of the application, "annealing" is understood to mean the combined action of forced forming by pressing the balloon against the balloon mold and heating to a temperature or the maintenance of the temperature in the fourth step of the method according to the invention.

The annealing step is preferably used to break down the high stresses in the balloon wall resulting from the blow molding process. Without the annealing step, the balloon can shrink excessively following storage or under the action of increased temperature and would lose its shape.

The annealing does not influence the original wall thickness distribution in the balloon, but rather its response to a mechanical load.

In accordance with a preferred embodiment of the invention, the mold consists of a cylindrical part and two cones, wherein at least one of the cones is movable in the cylindrical part in such a way that the distance between both cones can be changed. The mold particularly preferably has two movable cones in a cylindrical part, which are slid together more closely in the third step of the method.

A balloon as is used in angioplasty has to be substantially cylindrical for its function. This balloon shape is achieved by the mold used. The substantially cylindrical middle of the balloon is shaped by the cylindrical part, and the two movable cones form the conical end regions of the balloon, which serve for the connection to the catheter, in particular the balloon lumen. In the simplest form, the cylinder of the mold is expediently a tube with an inner diameter that corresponds to the target diameter of the balloon. The movable cones can consist of metal for example and each have openings in the middle, through which the tubular part of the blank is guided and through which the blank can be acted on by a pressurized fluid. The blank is fixed in the mold by the two cones. The strength with which the cones can be pushed together (the extent to which the length of the mold is reduced) is dependent on the (visco)elastic capability of the material to be able to relax again in the second step directly after the first step of the molding process.

The blank is expediently heated to a temperature above the glass transition temperature, preferably 30° C. above the glass transition temperature, particularly preferably 20° C. above the glass transition temperature. The temperature to be selected in each case is dependent on the glass transition temperature and the melting point of the material used. The selected temperature here must lie above the glass transition temperature and below the melting point of the material. Here, the blank can either be heated at least in part prior to the introduction into the mold. However, the heating of the blank in the mold by heat radiation is preferred, wherein the mold itself is preferably heated for this purpose.

Here, it is advantageous for the pressure in the first step to be maintained for a short period of time, preferably 0.1 s to 5 s, particularly preferably 0.1 s to 3 s, in particular 0.1 s to 1 s. Here, the pressure is applied until it is ensured that the blank bears completely against the inner wall of the mold in the first blow cycle (in the first step). Under this condition, the pressure is maintained for a period of time that is as short as possible, since the resilient recovery capability of the balloon material reduces with increasing duration of the maintenance of the pressure.

In the fourth step of the method according to the invention, the pressure is advantageously maintained for longer than in the first step of the method according to the invention. Here, higher temperatures than in the first step of the method according to the invention may also be advantageous. The times for the maintenance of the pressure and the temperatures in the fourth step of the method according to the invention correspond here to expedient times and temperatures of a blow molding method according to the prior art and are known to a person skilled in the art for the respective materials. Here, the temperature is basically held above the glass transition temperature and below the melting point. In addition, if the pressure is maintained, reference is made to what is known as "annealing". The combination of increased chain movability and mechanical load allows the controlled sliding of the chains directed toward one another until the chains are arranged in a most tightly packed manner relative to one another and thus crystallize. Regions crystallized in this way are dimensionally more stable than the adjacent amorphous regions, which have frozen stresses and want to contract upon heating.

After the fourth step, the blank is cooled below the glass transition temperature and removed from the mold (that is to say the pressure is reduced) without deforming further during this process. This also corresponds to the method in accordance with a blow molding method according to the prior art with a blowing step. The corresponding parameters are known to a person skilled in the art.

All viscoelastic polymers that allow blow molding, in particular polyamide, in particular PA12, polyether block amide, polyurethane, PET or PEBAX, can be considered as material for the blank and thus for the balloon.

In an expedient embodiment of the invention, a blank made of polyamide is used. Polyamide can be acted on with pressure ("blown") from a temperature of 48° C. and can be annealed up to a temperature of 178° C. Here, lower temperatures require longer annealing times and are less cost-effective accordingly. With use of a blank made of polyamide 12, the cones in the third step of the method according to the invention can be pushed together as far as 70% of their original spacing in the first step of the method. Here, the mold was heated to a temperature of 140° C. Here, in the first step of the method, the pressure is maintained for less than 1 s. It has been found in this exemplary embodiment of the invention that the blank can be shaped again without difficulty in a range between 70% and 100% of the original length (and thus of the original spacing of the cones in the first step of the method according to the invention) in the fourth step of the method according to the invention (that is to say, when acted on with pressure, the blank again bears completely in the fourth step against the inner wall of the mold changed in this way). Accordingly, the wall thickness in this expedient exemplary embodiment of the invention in the middle cylindrical region of the balloon produced in this way can increase in a range between 30% (when the cones are pushed together to 70% of their original spacing) and 0% (when the cones are not pushed together). In the exemplary embodiment of a blank made of polyamide, temperatures of 140° C. and a maintenance of the pressure between 15 s and 120 s, preferably for 20 s, are expedient in the fourth step.

The material of the blank advantageously experiences an axial stretching of less than 250%, preferably less than 215%, particularly preferably between 170% and 250%, in the cylindrical region of the mold as the method according to the invention is carried out.

Within the scope of the invention, the axial stretching is understood to mean the elongation in the axial direction by which the blank has been stretched in the axial direction during production. The radial stretching is accordingly the elongation to which the blank has been stretched in the radial direction.

Here, the following is true:

$$\varepsilon_{ax} = \frac{Q_R}{Q_B}$$

axial stretching during blow molding
with $$Q_R = \frac{\pi}{4}(d_a^2 - d_i^2)$$

cross section of the blank $$Q_B = \frac{\pi}{4}(D_a^2 - D_i^2) \approx \pi D_a s_B$$

cross section of the balloon $$\varepsilon_{rad,i} = \frac{D_{B,i}}{d_{R,i}}$$

radial stretching on the inner side during blow molding

The cross section corresponds to the total wall area of the blank or of the balloon when the blank or the balloon is cut once in a plane perpendicular to the longitudinal axis. The cross section thus forms the cross-sectional area of the blank or balloon consisting of material. Here, in the formulas:

d stands for the diameter of the blank (outer or inner)
D stands for the diameter of the balloon (outer or inner)
s stands for the wall thickness of the balloon
$\varepsilon_{rad}$ stand for the radial stretching, and
$\varepsilon_{ax}$ stands for the axial stretching,
the index B stands for balloon, the index R for blank, the index a for outer and the index i for inner.

The diameter d of the blank and the diameter D of the balloon are measured here at the respective point with a pressure application of 3 bar. When determining the diameter, the pressure has to be selected to be so high that the balloon completely unfolds, but is not stretched. The diameters of the conical end regions are accordingly substantially independent of the applied pressure.

In the case of a method according to the prior art, a blank experiences an axial stretching in the conical end regions of approximately 220%, and in the middle cylindrical region an axial stretching between 250% and 350%.

In the method according to the invention, a blank advantageously experiences an axial stretching in the conical end regions similar to that experienced in a method according to the prior art, but a much smaller axial stretching in the middle, cylindrical region.

Due to this advantageous embodiment of the invention, the ratio of the wall thickness in the middle cylindrical region to the wall thickness in the conical end region changes in the case of a balloon produced in this way. With constant wall thickness in the cylindrical region, as is the case with a balloon produced by a blow molding method of the prior art, a wall thickness that is reduced by up to 25% can be achieved in the conical end regions in the case of a balloon produced in accordance with this embodiment of the method.

This embodiment of the invention is suitable in particular for the production of balloons for balloon catheters, of which the use requires a high application of pressure by means of fluid, that is to say for the production of balloons that are particularly resistant to high pressure. The fatigue strength of balloons can be increased by an increase of the cross section, in particular an increase of the wall thickness. In order to increase the wall thickness, either the inner diameter can be reduced or the outer diameter can be increased. Both measures are subject to limits in the case of a blow molding method according to the prior art. With a strong reduction of the inner diameter, there is a risk of exceeding the yield strength of the inner balloon layer. Accordingly, the reject rate in the balloon production increases. In a blow molding method according to the prior art, the outer layer of the blank is always stretched to a lesser extent than the inner side. This stretch difference increases with increasing wall thickness. This lower stretch of the outer side increases the risk that a lower orientation along the peripheral direction, that is to say a lower radial orientation, is produced in the polymer material. This limits the stress that such an outer side can bear to the yield stress. Accordingly, the maximum pressure of the balloon produced in this way is limited.

In this embodiment of the invention, the method according to the invention increases the radial stretching of the outer side compared with the prior art. The higher radial stretching on the outer side compared with the prior art increases the radial orientation of the material also on the outer side and thus increases the pressure load-bearing capacity of the balloon produced in this way. This is made possible by the method according to the invention, which comprises two successive applications of pressure to the blank in a mold, of which the three-dimensional expansion is changed between pressure applications.

In particular, the blank in this embodiment of the invention experiences an outer radial stretching of more than 300%, in particular of more than 315%.

In a further advantageous embodiment of the invention, the blank on the inner side in the middle, cylindrical part experiences a radial stretching of less than 600%, preferably less than 550%, in particular less than 517%.

This embodiment of the invention is suitable in particular for producing balloons with high axial extensibility, that have an extensibility increased by 10%, in particular by 20%, compared with a balloon produced by means of a blow molding method according to the prior art. This embodiment of the invention is particularly suitable for the angioplasty of very strongly curved bodily vessels. Both during the expansion of the vessel and during the implantation of a support structure into a strongly curved bodily vessel of this type, there is an undesirable straightening of the bodily vessel caused by the expansion of a balloon according to the prior art. The unphysiological cylinder shape of the balloon is usually forced on the bodily vessel. A balloon according to the above-presented embodiment of the invention avoids this straightening effect of the bodily vessel by the expansion of the balloon. Due to the higher axial extensibility of the balloon of this embodiment of the invention, the balloon can also follow more easily the physiological course of the curved vessel, even in the expanded state.

In terms of the device, the stated object is achieved by a balloon suitable for use in a catheter for carrying out a method for angioplasty, consisting of a middle cylindrical region and two end regions delimiting the middle cylindrical region, said balloon having a ratio of the cross section in the middle region to the cross section in the end region of at least 2, in particular of greater than 3, in the event of a pressure application of 6 bar.

The balloon according to the invention differs considerably from the prior art. No other balloon according to the prior art has such a ratio of the cross section in the middle, cylindrical region to the cross section of the end region and consists here of a material piece that has not been subjected to any material-removing process.

A balloon having such a cross section can be produced in particular by the method according to the invention. Here, in particular a high proportion of the material is slid by steps 3 and 4 into the middle substantially cylindrical region. A balloon of this type is characterized by a very high bursting pressure. A balloon with such a wall thickness cannot be produced by any known method of the prior art without simultaneously also generating very thick conical end regions or without fusing together a number of balloons to form a single balloon.

The balloon particularly preferably consists of one piece and has a balloon wall thickness of 0.025 mm and an outer diameter of 3 mm.

The balloon expediently consists of polyamide, in particular PA12, polyether block amide, polyurethane, PET and/or PEBAX.

The balloon produced by the method according to the invention or an embodiment thereof is preferred.

FIGS. 1A-1D schematically illustrated the preferred method according to the invention. A tubular blank 1 is first introduced into the mold, which consists of a cylinder 3 and two cones 2 movable therein. The blank 1 is heated in the mold to a temperature above the glass transition temperature of the blank material. In this exemplary embodiment of the invention, the blank 1 is heated in the mold, wherein the heating is performed via the mold. A heating of the blank prior to the introduction into the mold is also possible here. Any method known to a person skilled in the art can be applied for the heating in or outside the mold.

Figure 1A:
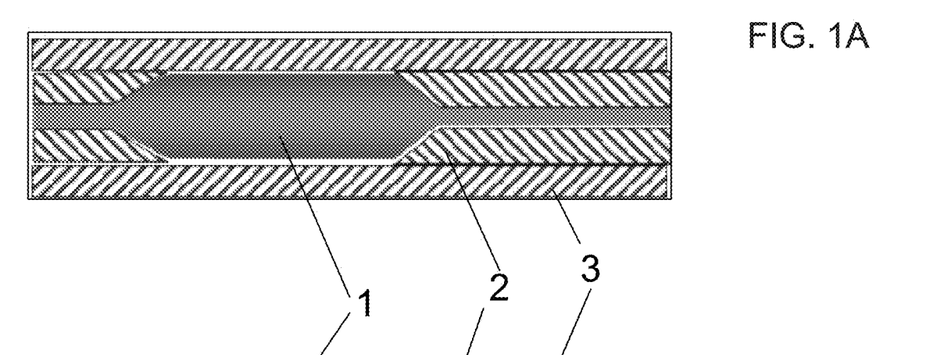
Figure 1B:
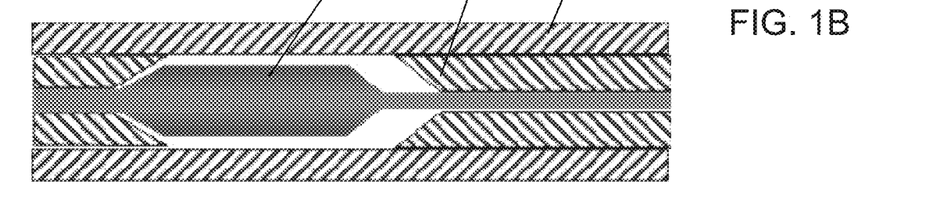
Figure 1C:
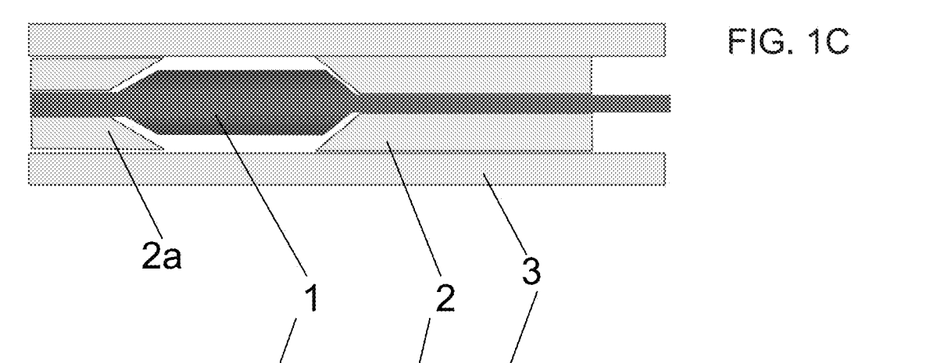

In the first step of FIG. 1A, the heated blank 1 is acted on with pressure in such a way that it nests completely against the inner wall of the mold. The inner wall of the mold is formed by the inner wall of the cylinder 3 and the inner wall of the two cones 2. In the next step of FIG. 1B, the blank 1 is relaxed again, that is to say the blank is no longer acted on with pressure. The blank 1 thus returns in part into its original expansion and loses the contact with the inner walls of the mold. In the third step of FIG. 1C, the three-dimensional volume of the mold is changed, by reducing the distance separating the two cones 2. The inner surface, against which the blank could nest during pressure application, is therefore changed in FIG. 1C. In this example embodiment of the invention, the right-hand cone 2 is slid closer to the left-hand cone 2a. The inner surface and the volume that can be taken up by the blank 1 are thus reduced with renewed pressure application in the step of FIG. 1D.

In the illustrated steps of FIGS. 1A to 1D, the blank 1 is held permanently at a temperature above the glass transition temperature of the material. The pressure application of the blank 1 in the step of FIG. 1A is performed over a period of time that is as short as possible. It is maintained until the complete contact of the blank 1 with the inner face of the mold is ensured. However, the pressure in the step of FIG. 1A is only maintained for such a period that the resilient recovery capability of the material is impaired to a minimal extent or, optimally, is not impaired at all. In the step if FIG. 1D, the pressure is maintained for much longer. Here, the pressure is maintained until an orientation in a material of the blank is produced and crystallizes. Here, a higher temperature than in the step of FIG. 1A can be selected as necessary. The balloon now produced is then removed from the mold (pressure reduction), and the balloon is cooled below the glass transition temperature.

Figure 1D:
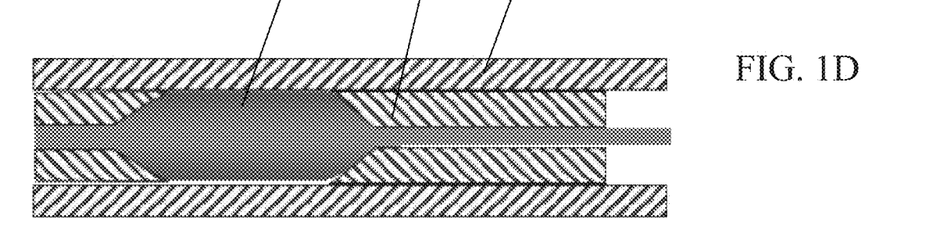

The pressure in the step of FIG. 1D can be substantially equal to a pressure application in a blow molding method according to the prior art. The blow molding method presented here can also be configured as a stretch blow molding method, that is to say an additional tensile force can be exerted on the blank in the axial direction (for example by a weight) during steps of FIGS. 1A-D.

Figure 2A:
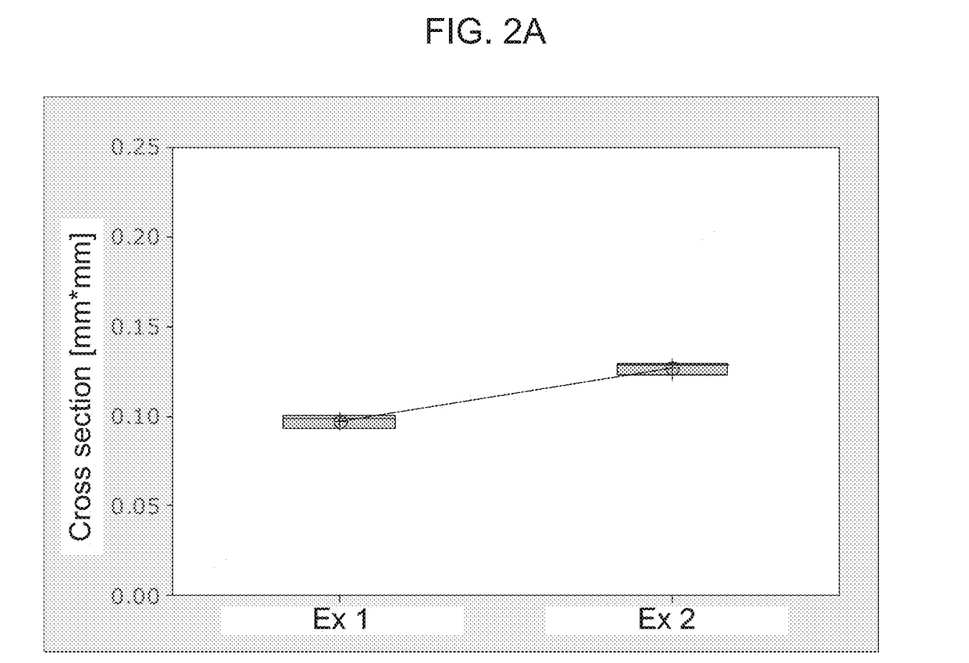
FIGS. 2A & 2B show a comparison of the cross sections in the middle cylindrical region and in the conical end region of a balloon produced by a method of the prior art and by an exemplary embodiment of the method according to the invention.
Figure 2B:
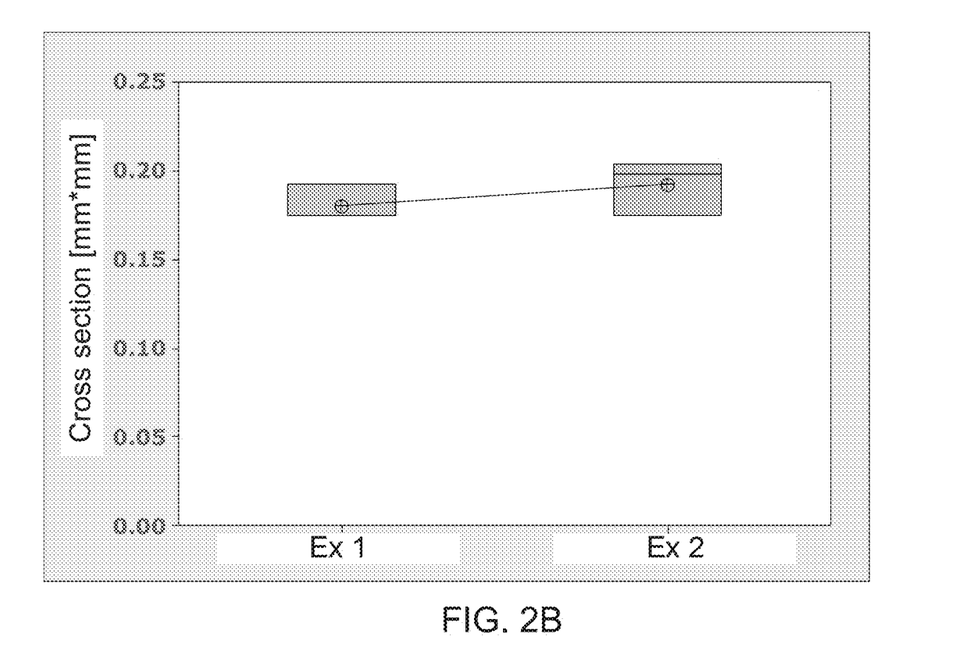

FIGS. 2A and 2B show a comparison of the cross sections of a balloon according to the prior art (Ex 1) and of a balloon (Ex 2) as has been produced by an exemplary embodiment of the method according to the invention.

Example 1 is a balloon in accordance with a blow molding method according to the prior art. Here, a tubular blank made of PA12 is heated to a temperature of 140° C. in a mold similar to the mold from FIG. 1. The heated blank is acted on with pressure for 25 s and is then removed from the mold and cooled below the glass transition temperature. The diameter of the mold in the cylindrical part is 3 mm, such that a balloon with 3 mm diameter is produced as product.

Example 2 is a balloon in accordance with a blow molding method according to the invention. Here too, a tubular blank made of PA12 is heated in a mold similar to the mold in FIG. 1. In contrast to Example 1, the blank according to Example 2 is acted on with pressure in the step if FIG. 1A for less than 1 s at 140° C. Following pressure reduction and relaxation of the blank in the step of FIG. 1B, the cones are slid together in the step of FIG. 1C to approximately 75% of their original spacing. The blank is then acted on again with pressure in the step of FIG. 1D at 140° C. for 20 s. The blank is then removed from the mold and cooled below the glass transition temperature. The diameter of the mold in the cylindrical part was also 3 mm in Example 2, such that a balloon with 3 mm diameter is also produced here.

FIGS. 2A and 2B show comparisons of the cross sections of the balloons in the middle cylindrical region (FIG. 2A) and a comparison of the cross sections in the conical end region (FIG. 2B) for Examples 1 (Ex 1) and 2 (Ex 2). Here, in Example 2 the cross section and therefore also the wall thickness in the middle balloon portion increase significantly compared with Example 1 according to the prior art. With similar wall thicknesses in the conical end region of the balloon, an increase of the wall thickness in the middle region of 27% can be achieved with the balloon according to the exemplary embodiment of the invention (Example 2). The balloon according to Example 2 achieves a ratio of the cross section in the middle region to the cross section in the conical neck region of 3:1 with pressure application with 6 bar.

Figure 3A:
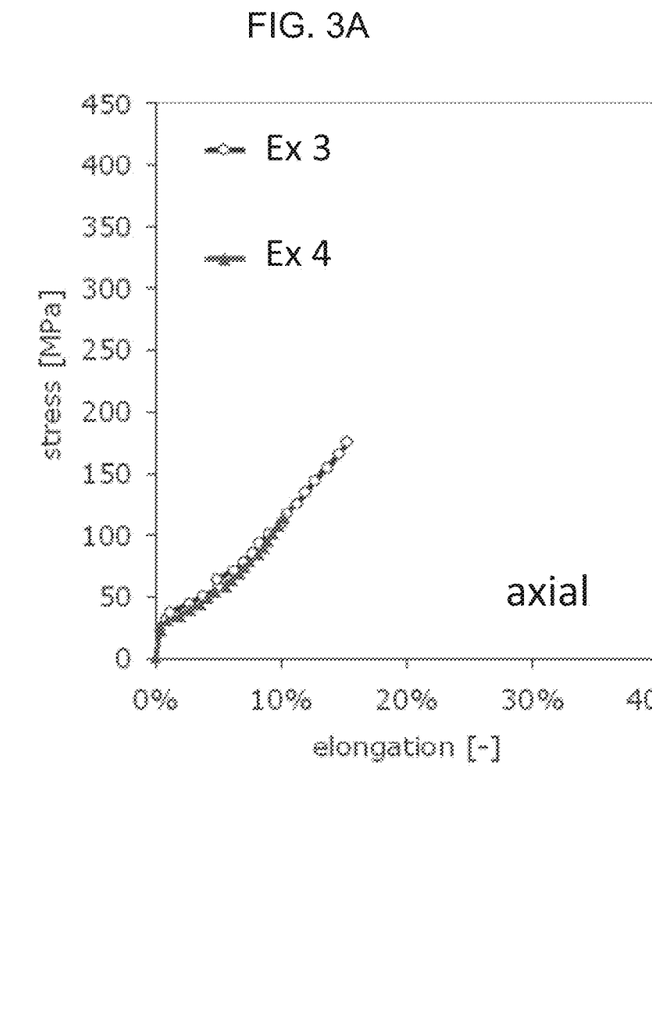
FIGS. 3A and 3B show a comparison of the radial and axial stresses over the elongation of a balloon according to the prior art compared with a balloon according to an exemplary embodiment of the method according to the invention.
Figure 3B:
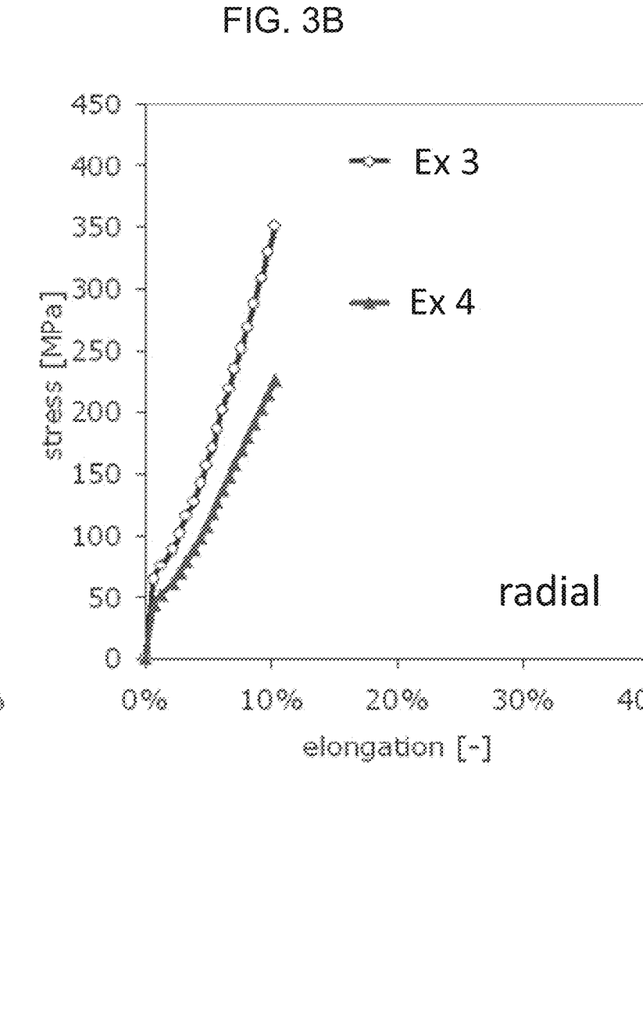

FIGS. 3A and 3b compare the stress/elongation behavior between a balloon according to the prior art (Ex 3) and a balloon (Ex 4) as has been produced by an exemplary embodiment of the method according to the invention.

Example 3 is a balloon in accordance with a blow molding method according to the prior art. Here, a tubular blank with the dimensions 0.57×1.07 made of PA12 is heated to a temperature of 140° C. in a mold similar to the mold from FIG. 1. The heated blank is acted on with pressure for 25 s and is then removed from the mold and cooled below the glass transition temperature. The diameter of the mold in the cylindrical part is 3.5 mm, such that a balloon with 3.5 mm diameter is produced as product.

Example 4 is a balloon in accordance with a blow molding method according to the invention. Here too, a tubular blank with dimensions 0.57×1.07 made of PA12 is heated in a mold similar to the mold in FIG. 1. In contrast to Example 3, the blank according to Example 2 is acted on with pressure in the step of FIG. 1A for less than is at 140° C. After pressure reduction and relaxation of the blank in the step of FIG. 1B, the cones are pushed together in the step of FIG. 1C to approximately 75% of their original spacing. The blank is then acted on again with pressure at 140° C. for 20 s in the step of FIG. 1D. The blank is then removed from the mold and cooled below the glass transition temperature. The diameter of the mold in the cylindrical part in Example 2 was also 3.5 mm, such that a balloon with 3.5 mm diameter is also produced here.

FIG. 3 shows a comparison of the stress/elongation behavior in the axial direction (FIG. 3A) and in the radial direction (FIG. 3B) for Examples 3 (Ex 3) and 2 (Ex 4). Here, the axial elongation of the balloon in Example 4 decreases compared with Example 3 according to the prior art. With the same starting tube, a reduction of the axial balloon compliance from 15% (ex 3) to 11% (ex 4) can be achieved with the balloon according to the exemplary embodiment of the invention (Example 4). The reduced axial elongation ensures lower stresses axially and radially at constant pressure, without having changed here the radial compliance behavior of the balloon.

Figure 4A:
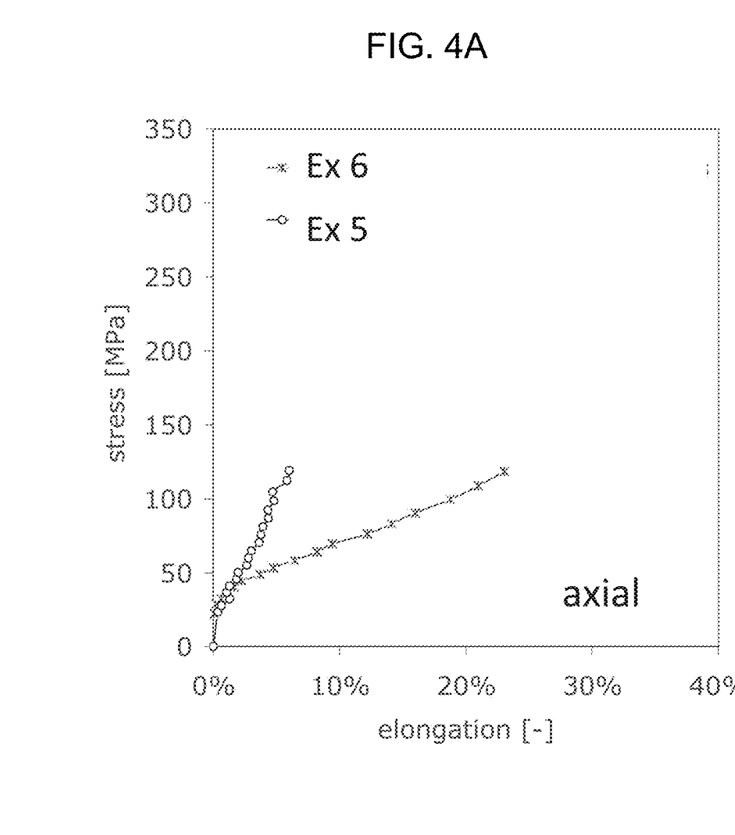
FIGS. 4A and 4B show a comparison of the radial and axial stresses over the elongation of a balloon according to the prior art compared with a balloon according to another exemplary embodiment of the method according to the invention.
Figure 4B:
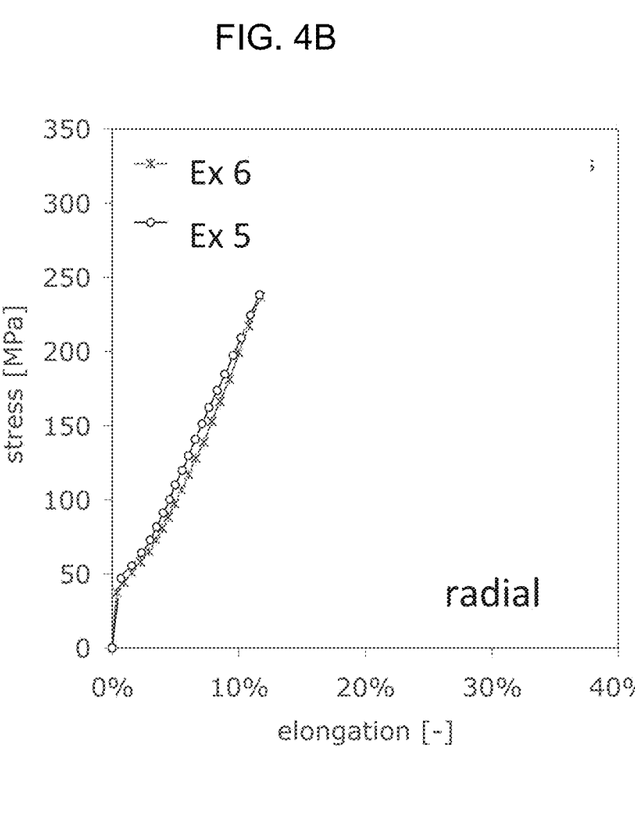

FIGS. 4A and 4B compare the stress/elongation behavior between a balloon according to a prior art (Ex 5) and a balloon (Ex 6) as has been produced by an exemplary embodiment of the method according to the invention.

Example 5 is a balloon in accordance with a blow molding method according to the prior art. Here, a tubular blank with the dimensions 0.58×0.92 made of PA12 is heated to a temperature of 140° C. in a mold similar to the mold from FIG. 1. The heated blank is acted on with pressure for 25 s and is then removed from the mold and cooled below the glass transition temperature. The diameter of the mold in the cylindrical part is 3.0 mm, such that a balloon with 3.0 mm diameter is produced as product.

Example 6 is a balloon in accordance with a blow molding method according to the invention. Here too, a tubular blank with the dimensions 0.58×0.92 made of PA12 is heated in a mold similar to the mold in FIG. 1. In contrast to Example 3, the blank according to Example 2 is acted on with pressure for less than 1 s at 140° C. in the step of FIG. 1A. Following pressure reduction and relaxation of the blank in the step of FIG. 1B, the cones are pushed together in the step of FIG. 1C to approximately 75% of their original spacing. The blank is then acted on again with pressure in the step of FIG. 1D at 140° C. for 20 s. The blank is then removed from the mold and cooled below the glass transition temperature. The diameter of the mold in the cylindrical part was also 3.0 mm in Example 2, such that a balloon with 3.0 mm diameter is also produced here.

FIG. 4 shows a comparison of the stress/elongation behavior in the axial direction (FIG. 4A) and in the radial direction (FIG. 4B) for Examples 5 (Ex 5) and 6 (Ex 6). Here, the axial extensibility of the balloon increases in Example 6 compared with the example according to the prior art (ex 5). With identical starting tube, an increase of the axial balloon compliance from 7% (ex 5) to 23% (ex 6) can be achieved with the balloon according to the exemplary embodiment of the invention (Example 6). In spite of increased axial elongation, the balloons (ex 6) do not reach the same stress state as the standard balloons (ex. 5) until 24 bar, since only at this pressure has the balloon used its axial elongation reserve established by the method according to the invention.

What is claimed is:

1. A method for producing a balloon from a suitable blank, wherein the blank is introduced into a mold, comprising:
    heating the blank and first expanding with pressure to expand it against an inner wall of the mold,
    after said first expanding, reducing the pressure to relax the blank away from the inner wall,
    after said reducing, changing the three-dimensional volume of the mold by reducing a length of the mold, wherein the mold consists of a cylindrical part and two cones, wherein at least one of the cones is movable in the cylindrical part in such a way that the distance between both cones can be changed during said changing,
    after said changing, second expanding the blank with pressure again to expand it against the inner wall of the changed volume of the mold.

2. The method as claimed in claim 1, wherein said reducing a length comprises sliding the two movable cones closer.

3. The method as claimed in claim 1, wherein said heating comprises heating to a temperature above the glass transition temperature.

4. The method as claimed in claim 1, wherein the pressure in said first expanding is maintained for 0.1 s to 5 s.

5. The method as claimed in claim 3, wherein the temperature above the glass transition temperature is 20° C. above the glass transition temperature.

6. The method as claimed in claim 4, wherein the pressure in said first expanding is maintained for 0.1 s to 3 s.

7. The method as claimed in claim 6, wherein the pressure in said first expanding is maintained for 0.1 s to 1 s.

8. The method as claimed in claim 1, wherein said first expanding is conducted for a short enough period of time to maintain resilient recovery capability of material of the blank and said second expanding is conducted for a long enough time to crystallize the material of the blank.

9. The method as claimed in claim 8, wherein the blank is maintained above glass transition temperature until completion of the second expanding.

10. A method for producing a balloon from a suitable blank, wherein the blank is introduced into a mold, comprising:
heating the blank and first expanding with pressure to expand it against an inner wall of the mold,
after said first expanding, reducing the pressure to relax the blank away from the inner wall,
after said reducing, changing the three-dimensional volume of the mold by reducing a length of the mold, wherein said reducing a length comprises reducing the axial length of the mold to 70-75% of its length in the first expanding,
after said changing, second expanding the blank with pressure again to expand it against the inner wall of the changed volume of the mold.

11. The method as claimed in claim 1, wherein the temperature is raised higher during the second expanding compared to said first expanding.

12. The method as claimed in claim 10, wherein the mold consists of a cylindrical part and two cones, wherein at least one of the cones is movable in the cylindrical part in such a way that the distance between both cones can be changed during said changing.

13. The method as claimed in claim 12, wherein said reducing a length comprises sliding the two movable cones closer.

14. The method as claimed in claim 10, wherein said heating comprises heating to a temperature above the glass transition temperature.

15. The method as claimed in claim 10, wherein the pressure in said first expanding is maintained for 0.1 s to 5 s.

16. The method as claimed in claim 10, wherein said first expanding is conducted for a short enough period of time to maintain resilient recovery capability of material of the blank and said second expanding is conducted for a long enough time to crystallize the material of the blank.

17. The method as claimed in claim 16, wherein the blank is maintained above glass transition temperature until completion of the second expanding.

* * * * *